(12) United States Patent
Lee et al.

(10) Patent No.: US 9,422,417 B1
(45) Date of Patent: Aug. 23, 2016

(54) MODIFIED CONJUGATED DIENE POLYMER, METHOD FOR PREPARING THE SAME AND RUBBER COMPOSITION COMPRISING THE SAME

(71) Applicant: LG CHEM, LTD., Seoul (KR)

(72) Inventors: Sang Mi Lee, Daejeon (KR); Kyoung Hoon Kim, Daejeon (KR); Young Chel Choi, Daejeon (KR); Ro Mi Lee, Daejeon (KR); Heung Yeal Choi, Daejeon (KR); Moon Seok Chun, Daejeon (KR)

(73) Assignee: LG Chem, Ltd., Seoul (KR)

(*) Notice: Subject to any disclaimer, the term of this patent is extended or adjusted under 35 U.S.C. 154(b) by 249 days.

(21) Appl. No.: 14/381,123

(22) PCT Filed: Sep. 3, 2013

(86) PCT No.: PCT/KR2013/007915
§ 371 (c)(1),
(2) Date: Aug. 26, 2014

(87) PCT Pub. No.: WO2015/034110
PCT Pub. Date: Mar. 12, 2015

(51) Int. Cl.
*C08J 3/24* (2006.01)
*C08K 3/36* (2006.01)
*C08F 236/14* (2006.01)
*C08K 3/04* (2006.01)
*C07F 7/18* (2006.01)

(52) U.S. Cl.
CPC ............... *C08K 3/36* (2013.01); *C07F 7/1836* (2013.01); *C08F 236/14* (2013.01); *C08K 3/04* (2013.01)

(58) Field of Classification Search
CPC ...... C08J 2325/10; C08F 36/06; C08L 101/10
See application file for complete search history.

(56) References Cited

U.S. PATENT DOCUMENTS

| 2005/0020757 A1* | 1/2005 | Ozawa ................... B60C 1/00 524/492 |
| 2007/0185267 A1 | 8/2007 | Kobayashi et al. |

FOREIGN PATENT DOCUMENTS

| CN | 1599758 A | 3/2005 |
|---|---|---|
| JP | 2004-018795 | 1/2004 |
| JP | 2004018795 A | 1/2004 |
| JP | 2011006543 A | 1/2011 |
| JP | 2011144349 A | 7/2011 |
| KR | 10-2002-0095212 | 12/2002 |
| KR | 10-2003-0083736 | 10/2003 |
| KR | 10-2007-0017122 | 2/2007 |
| KR | 10-2011-0070871 | 6/2011 |
| KR | 1020110070871 A | 6/2011 |
| KR | 10-2013-0018729 | 2/2013 |
| KR | 10-2013-0059360 | 6/2013 |
| WO | 2010-044252 | 4/2010 |
| WO | 2010044252 A1 | 4/2010 |
| WO | 2011-125698 | 10/2011 |
| WO | 2011-155326 | 12/2011 |

* cited by examiner

*Primary Examiner* — Kuo-Liang Peng
(74) *Attorney, Agent, or Firm* — Dentons US LLP

(57) ABSTRACT

Disclosed is a modified conjugated diene polymer represented by Formula 1. Advantageously, provided are a modified conjugated diene polymer which exhibits superior compatibility with a reinforcing filler, heat generation, tensile strength and abrasion resistance, low fuel consumption and excellent wet skid resistance, a method for preparing the same and a rubber composition comprising the same.

18 Claims, No Drawings

MODIFIED CONJUGATED DIENE POLYMER, METHOD FOR PREPARING THE SAME AND RUBBER COMPOSITION COMPRISING THE SAME

This application is a National Stage Entry of International Application No. PCT/KR2013/007915, filed Sep. 3, 2013, which is hereby incorporated by reference in its entirety for all purposes as if fully set forth herein.

TECHNICAL FIELD

The present invention relates to a modified conjugated diene polymer, a method for preparing the same and a rubber composition comprising the same. The present invention relates to a modified conjugated diene polymer which exhibits superior compatibility with a reinforcing filler, heat generation, tensile strength and abrasion resistance, low fuel consumption and excellent wet skid resistance, a method for preparing the same and a rubber composition comprising the same.

BACKGROUND ART

Concerns about environments including inhibition of carbon dioxide are socially demanded. As such, there is a growing demand for low fuel consumption of vehicles. Accordingly, there is an increasing demand for materials having superior wet skid resistance, abrasion resistance and breaking strength as materials for vehicle tires, in particular, tire treads contacting the roads.

Meanwhile, carbon black, silica and the like are used as reinforcing fillers for tire treads. When silica is used as a reinforcing filler, advantageously, hysteresis loss is reduced or wet skid resistance is improved. As compared to carbon black having a hydrophobic surface, silica having a hydrophilic surface has a disadvantage of low dispersibility of silica in rubbers due to low affinity to conjugated diene rubbers. Accordingly, use of additional silane coupling agent is required to improve dispersibility of silica in rubbers or form silica-rubber bonds.

In order to solve these problems, functional groups having affinity or reactivity to silica are introduced into an end of rubber molecules to improve dispersibility of silica in conjugated diene rubbers and implement sealing through bonding between the end of rubber molecules and silica particles and thereby reduce hysteresis loss.

DISCLOSURE

Technical Problem

Therefore, as a result of extensive research to address the problems of the related art, the present inventors discovered that silica used as a reinforcing filler provides a modified conjugated diene polymer which exhibits superior compatibility, heat generation, tensile strength and abrasion resistance, low fuel consumption and excellent wet skid resistance, and a rubber composition comprising the same. The present invention has been completed based on this discovery.

It is one object of the present invention to provide a modified conjugated diene polymer which exhibits superior compatibility with an inorganic filler, heat generation, tensile strength and abrasion resistance, low fuel consumption and excellent wet skid resistance.

It is another object of the present invention to provide a method for preparing the modified conjugated diene polymer.

It is another object of the present invention to provide a rubber composition comprising the modified conjugated diene polymer and a tire comprising the rubber composition.

It is yet another object of the present invention to provide a modifying agent used for preparation of the modified conjugated diene polymer.

The above and other objects can be accomplished by the present disclosure given below.

Technical Solution

In accordance with one aspect of the present invention, provided is a modified conjugated diene polymer represented by the following Formula 1:

[Formula 1]

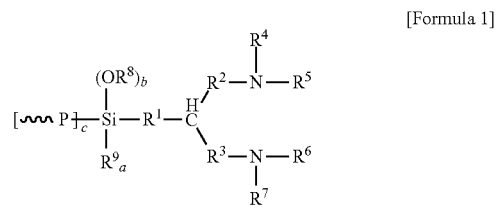

wherein $R^1$, $R^2$ and $R^3$ represent an alkylene group ($-(CH_2)_n-$, n=1~15), $R^4$, $R^5$, $R^6$, $R^7$ and $R^9$ each independently represent an alkyl group or an alkylsilyl group, $R^8$ represents a $C_1$-$C_{15}$ alkyl group, and P is a conjugated diene polymer chain.

In Formula 1, a is an integer of 0 to 2, b is an integer of 0 to 2, and c is an integer of 1 to 3 with the proviso that a+b+c equals 3.

In Formula 1, the conjugated diene polymer chain is a conjugated diene monomer, or a copolymer of a conjugated diene monomer and an aromatic vinyl monomer.

In accordance with another aspect of the present invention, provided is a method for preparing a modified conjugated diene polymer comprising (a) polymerizing a conjugated diene monomer, or a mixture of a conjugated diene monomer and an aromatic vinyl monomer in the presence of a solvent containing an organometallic compound to prepare an active conjugated diene polymer having a metal end, and (b) modifying the active conjugated diene polymer with a compound represented by the following Formula 2 as a modifying agent:

[Formula 2]

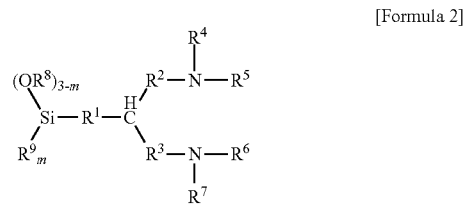

wherein $R^1$, $R^2$ and $R^3$ represent an alkylene group ($-(CH_2)_n-$, n=1~15), $R^4$, $R^5$, $R^6$, $R^7$ and $R^9$ each independently represent an alkyl group or an alkylsilyl group, $R^8$ represents a $C_1$-$C_{15}$ alkyl group and m is an integer of 0 to 2.

In accordance with another aspect of the present invention, provided is a rubber composition comprising 0.1 to 200 parts by weight of a reinforcing filler with respect to 100 parts by weight of the modified conjugated diene polymer.

In accordance with another aspect of the present invention, provided is a tire comprising the rubber composition.

In accordance with yet another aspect of the present invention, provided is a modifying agent used for preparation of the modified conjugated diene polymer.

Advantageous Effects

As apparent from the foregoing, the rubber composition comprising the modified conjugated diene polymer according to the present invention, when mixed with silica as a reinforcing filler, advantageously, exhibits superior compatibility with a reinforcing filler, heat generation, tensile strength and abrasion resistance, low fuel consumption and excellent wet skid resistance.

Best Mode

Hereinafter, the modified conjugated diene polymer, the method for preparing the same, the rubber composition comprising the same, the tire comprising the rubber composition and the like will be described in detail.

The modified conjugated diene polymer according to the present invention comprises a polymer represented by the following Formula 1:

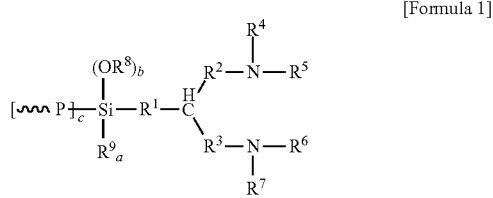

[Formula 1]

wherein $R^1$, $R^2$ and $R^3$ represent an alkylene group ($-(CH_2)_n-$, n=1~15), $R^4$, $R^5$, $R^6$, $R^7$ and $R^9$ each independently represent an alkyl group or an alkylsilyl group, $R^8$ represents a $C_1$-$C_{15}$ alkyl group, and P is a conjugated diene polymer chain.

In Formula 1, a is an integer of 0 to 2, b is an integer of 0 to 2 and c is an integer of 1 to 3 with the proviso that a+b+c equals 3.

$R^4$, $R^5$, $R^6$, $R^7$ and $R^9$ are for example an alkyl group or a $C_1$-$C_{15}$ alkyl group.

$R^1$, $R^2$ and $R^3$ are for example an alkylene group, preferably, a $C_1$-$C_{15}$ alkylene group.

In another example, $R^1$, $R^2$ and $R^3$ are a bivalent alkylsilyl group, preferably, a bivalent $C_1$-$C_{15}$ alkylsilyl group.

The alkylsilyl group according to the present invention is, for example, a linked group such as alkylene-silyl-alkylene, silyl-alkylene or alkylene-silyl.

The conjugated diene polymer chain is for example a conjugated diene monomer, or a copolymer of the conjugated diene monomer and an aromatic vinyl monomer.

In another example, the conjugated diene polymer chain may be a polymer chain comprising 0.0001 to 40% by weight, preferably 10 to 35% by weight, more preferably 20 to 30% by weight of the aromatic vinyl monomer, based on 100% by weight in total of the conjugated diene monomer and the aromatic vinyl monomer.

The conjugated diene polymer may be for example a random copolymer of the conjugated diene monomer and the aromatic vinyl monomer.

The conjugated diene monomer, for example, comprises at least one selected from the group consisting of 1,3-butadiene, 2,3-dimethyl-1,3-butadiene, piperylene, 3-butyl-1,3-octadiene, isoprene, and 2-phenyl-1,3-butadiene. In another example, the conjugated diene monomer may be 1,3-butadiene, but the present invention is not limited thereto.

The aromatic vinyl monomer, for example, comprises at least one selected from the group consisting of styrene, α-methylstyrene, 3-methylstyrene, 4-methylstyrene, 4-propylstyrene, 1-vinylnaphthalene, 4-cyclohexylstyrene, 4-(p-methylphenyl)styrene, and 1-vinyl-5-hexylnaphthalene. In another example, the aromatic vinyl monomer is styrene or α-methylstyrene, but the present invention is not limited thereto.

The modified conjugated diene polymer, for example, has a Mooney viscosity of 40 or higher, preferably 40 to 90, more preferably 45 to 85, most preferably 50 to 80.

The modified conjugated diene polymer, for example, has a number average molecular weight of 1,000 to 2,000,000 g/mol, preferably 10,000 to 1,000,000 g/mol, more preferably 100,000 to 500,000 g/mol.

The conjugated diene polymer, for example, has a vinyl content of 25% or higher, preferably 30 to 70%, more preferably 40 to 60%. Within this range, there are advantages in that glass transition temperature of the polymer is increased, properties, such as running resistance and brake power, required for produced tires are satisfied and fuel consumption is reduced.

The vinyl content means a content of a unit having a vinyl group, or a content of a 1,2-added conjugated diene monomer rather than a 1,4-added conjugated diene monomer with respect to 100% by weight of the conjugated diene monomer.

The modified conjugated diene polymer may, for example, have a polydispersity index (PDI) of 0.5 to 10, preferably 0.5 to 5, more preferably 1.0 to 2.0.

Regarding viscoelasticity, the modified conjugated diene polymer, for example, has a Tan δ at 0° C. (loss modulus at 0° C.), measured at 10 Hz by dynamic-mechanical analysis (DMA) after mixing with silica, of 0.6 to 1, preferably 0.9 to 1. Within this range, there is an effect in that skid resistance or wet skid resistance is greatly improved, as compared to the related art.

In addition, the modified conjugated diene polymer has, for example, a Tan δ at 60° C., of 0.06 to 0.09, preferably, 0.06 to 0.08. Within this range, rolling resistance or rotational resistance (RR) is advantageously greatly improved, as compared to the related art.

In addition, the present invention provides a method for preparing a modified conjugated diene polymer according to the present invention including (a) polymerizing a conjugated diene monomer, or a mixture of the conjugated diene monomer and an aromatic vinyl monomer in the presence of a solvent containing an organometallic compound to prepare an active conjugated diene polymer having a metal end, and (b) modifying the active conjugated diene polymer with a compound represented by the following Formula 2 as a modifying agent:

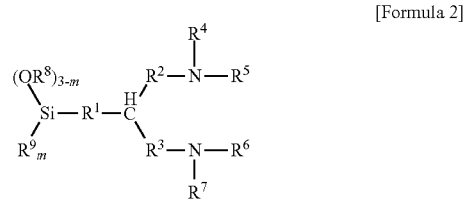

[Formula 2]

wherein $R^1$, $R^2$ and $R^3$ represent an alkylene group ($-(CH_2)_n-$, n=1~15), $R^4$, $R^5$, $R^6$, $R^7$ and $R^9$ each independently represent an alkyl group or an alkylsilyl group, $R^8$ represents a $C_1$-$C_{15}$ alkyl group and m is an integer of 0 to 2.

$R^1$ to $R^9$ are defined as above.

Polymerization

The conjugated diene polymer, which is an unmodified form of the modified conjugated diene polymer, is obtained by polymerizing a conjugated diene monomer, or copolymerizing the conjugated diene monomer with an aromatic vinyl monomer. Polymerization of the conjugated diene polymer may be carried out by adding a polymerization initiator to a reactor for copolymerization of the conjugated diene monomer or the conjugated diene monomer and the aromatic vinyl monomer.

The conjugated diene monomer, for example, comprises at least one selected from the group consisting of 1,3-butadiene, 2,3-dimethyl-1,3-butadiene, piperylene, 3-butyl-1,3-octadiene, isoprene, and 2-phenyl-1,3-butadiene. In another example, the conjugated diene monomer may be 1,3-butadiene, but the present invention is not limited thereto.

The aromatic vinyl monomer, for example, comprises at least one selected from the group consisting of styrene, α-methylstyrene, 3-methylstyrene, 4-methylstyrene, 4-propylstyrene, 1-vinylnaphthalene, 4-cyclohexylstyrene, 4-(p-methylphenyl)styrene, and 1-vinyl-5-hexylnaphthalene. In another example, the aromatic vinyl monomer is styrene or α-methylstyrene, but the present invention is not limited thereto.

The aromatic vinyl monomer may be present in an amount of 0.0001 to 40% by weight, preferably 10 to 35% by weight, more preferably 20 to 30% by weight, based on 100% by weight in total of the conjugated diene monomer and the aromatic vinyl monomer.

The solvent is for example hydrocarbon and preferably comprises at least one selected from the group consisting of n-pentane, n-hexane, n-heptane, isooctane, cyclohexane, toluene, benzene and xylene.

The organometallic compound is for example an organic alkali metal compound and preferably comprises at least one selected from the group consisting of organolithium compounds, organosodium compounds, organopotassium compounds, organorubidium compounds and organocesium compounds.

In another example, the organometallic compound may comprise at least one selected from the group consisting of methyl lithium, ethyl lithium, isopropyl lithium, n-butyl lithium, sec-butyl lithium, tert-butyl lithium, n-decyl lithium, tert-octyl lithium, phenyl lithium, 1-naphthyl lithium, n-eicosyl lithium, 4-butylphenyl lithium, 4-tolyl lithium, cyclohexyl lithium, 3,5-di-n-heptylcyclohexyl lithium and 4-cyclopentyl lithium.

In another example, the organometallic compound is selected from the group consisting of n-butyl lithium, sec-butyl lithium or a mixture thereof.

In another example, the organometallic compound may comprise at least one selected from the group consisting of naphthyl sodium, naphthyl potassium, lithium alkoxide, sodium alkoxide, potassium alkoxide, lithium sulfonate, sodium sulfonate, potassium sulfonate, lithium amide, sodium amide and potassium amide. The organometallic compound may be used in combination with another organometallic compound.

The organometallic compound is for example used in an amount of 0.01 to 10 mmol, preferably 0.05 to 5 mmol, more preferably 0.1 to 2 mmol, most preferably 0.1 to 1 mmol, based on 100 g in total of the monomer.

A molar ratio of the organometallic compound to the compound represented by Formula 2 is for example 1:0.1 to 1:10, preferably 1:0.5 to 1:2.

The active conjugated diene polymer having a metal end means a polymer wherein a polymer anion is bonded to a metal cation.

In the method for preparing a modified conjugated diene polymer according to the present invention, the polymerization may further comprise adding a polar additive.

The polar additive is for example a base. In another example, the polar additive is preferably selected from the group consisting of ether, amine or a mixture thereof, or is more preferably selected from the group consisting of tetrahydrofuran, ditetrahydrofurylpropane, diethylether, cycloamylether, dipropyl ether, ethylene methyl ether dimethyl ether, ethylene dimethyl ether, diethylene glycol, dimethyl ether, tertiary butoxyethoxyethane, bis(2-dimethylaminoethyl)ether, (dimethylaminoethyl)ethylether, trimethylamine, triethylamine, tripropylamine, tetramethylethylenediamine and mixtures of two or more thereof. Most preferred is ditetrahydrofurylpropane, triethylamine or tetramethylethylenediamine.

The polar additive may be for example used in an amount of 0.001 to 50 g, 0.001 to 10 g, 0.005 to 1 g, preferably 0.005 to 0.1 g, based on 100 g in total of the added monomer.

In another example, the polar additive may be used in an amount of 0.001 to 10 g, preferably 0.005 to 1 g, more preferably 0.005 to 0.1 g, based on 1 mmol in total of the added organometallic compound.

When the conjugated diene monomer is copolymerized with the aromatic vinyl monomer, a block copolymer may be readily prepared due to difference in reaction speed between the monomers. However, when the polar additive is added, reaction speed of the vinyl aromatic compound having a lower reaction speed than the conjugated diene monomer is increased, and variation of microstructure of the copolymer corresponding thereto, for example, synthesis of a random copolymer is advantageously induced.

The polymerization may be for example anionic polymerization.

In another example, the polymerization may be living anionic polymerization wherein active ends are obtained by growth reaction by anions.

The polymerization may be for example polymerization at an elevated temperature or polymerization at a fixed temperature.

The polymerization at an elevated temperature means a polymerization method which includes elevating a reaction temperature by heating after adding an organometallic compound. The polymerization at a fixed temperature means a polymerization method which does not include heating after adding an organometallic compound.

A temperature of the polymerization is for example −20 to 200° C., preferably 0 to 150° C., more preferably 10 to 120° C.

Modification

The modified conjugated diene polymer may be obtained by reacting the active conjugated diene copolymer obtained by the polymerization with the compound represented by Formula 2 as a modifying agent and the modifying agent may be a compound having a silyl group substituted by an alkoxy group and a nitrogen atom.

The modification may be for example carried out by adding one or more types, preferably, two or three types of the compound represented by Formula 2.

In addition, the modification may include reaction, for example, at 0 to 90° C. for one minute to 5 hours.

The method for preparing a modified conjugated diene polymer according to the present invention may be, for example, carried out by batch or continuous polymerization including one, two or more reactors.

The modified conjugated diene polymer may be, for example, prepared according to the method for preparing a modified conjugated diene polymer.

The rubber composition according to the present invention comprises 100 parts by weight of the modified conjugated diene polymer and 0.1 to 200 parts by weight of the reinforcing filler.

The rubber composition may further comprise, for example, another rubber.

The other rubber may be, for example, selected from the group consisting of styrene-butadiene rubber (SBR), butadiene rubber (BR), natural rubber and a mixture thereof.

The styrene-butadiene rubber (SBR) may be, for example, a solution styrene-butadiene rubber (SSBR).

The rubber composition according to the present invention may, for example, comprise 20 to 100 parts by weight of the modified conjugated diene polymer and 0.1 to 80 parts by weight of another rubber.

In another example, the rubber composition may comprise 20 to 99 parts by weight of the modified conjugated diene polymer and 1 to 80 parts by weight of another rubber.

In another example, the rubber composition may comprise 10 to 100 parts by weight of the modified conjugated diene polymer, 0.1 to 90 parts by weight of another rubber, 5 to 200 parts by weight of silica and 2 to 20 parts by weight of a silane coupling agent.

In another example, the rubber composition may further comprise 0.1 to 100 parts by weight of carbon black.

In another example, the rubber composition may comprise 10 to 100 parts by weight of the modified conjugated diene polymer, 0.1 to 90 parts by weight of another rubber, 5 to 200 parts by weight of silica and 2 to 20 parts by weight of a silane coupling agent, wherein the total weight of the modified conjugated diene polymer and the another conjugated diene polymer is 100 parts by weight.

The rubber composition according to the present invention may further comprise 0.1 to 100 parts by weight of carbon black.

In another example, the rubber composition according to the present invention may comprise 100 parts by weight of a polymer mixture comprising 10 to 100% by weight of the modified conjugated diene polymer and 0 to 90% by weight of the another conjugated diene polymer, 5 to 200 parts by weight of silica and 2 to 20 parts by weight of a silane coupling agent.

In another example, the rubber composition according to the present invention may further comprise 0.1 to 100 parts by weight of carbon black.

The reinforcing filler may be present in an amount of, for example, 10 to 150 parts by weight, preferably 50 to 100 parts by weight.

The reinforcing filler may be, for example, selected from the group consisting of carbon black, a silica filler and a mixture thereof.

In another example, the reinforcing filler may be silica. In this case, advantageously, dispersibility is greatly improved and hysteresis loss is greatly decreased because an end of the modified conjugated diene polymer is bonded to (or capped with) silica particles.

The rubber composition may for example further comprise 1 to 100 parts by weight of an oil.

The oil may be, for example, a mineral oil, a softening agent or the like.

The oil may be, for example, used in an amount of 10 to 100 parts by weight, preferably, 20 to 80 parts by weight, with respect to 100 parts by weight of the conjugated diene copolymer. Within this range, there are effects in that properties of the rubber composition are efficiently exhibited, the rubber composition is suitably softened and processability is thus excellent.

The rubber composition may be for example used as a material for tires or tire treads.

The tire may comprise the modified conjugated diene polymer rubber composition.

The modifying agent according to the present invention is represented by the following Formula 2:

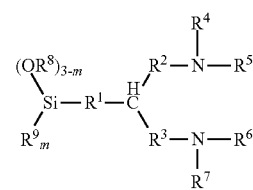

[Formula 2]

wherein $R^1$, $R^2$ and $R^3$ represent an alkylene group ($-(CH_2)_n-$, n=1~15), $R^4$, $R^5$, $R^6$, $R^7$ and $R^9$ each independently represent an alkyl group or an alkylsilyl group, $R^8$ represents a $C_1$-$C_{15}$ alkyl group and m is an integer of 0 to 2.

Hereinafter, preferred examples will be provided for better understanding of the present invention. It will be apparent to those skilled in the art that these examples are only provided to illustrate the present invention and various modifications and alterations are possible within the scope and technical range of the present invention. Such modifications and alterations fall within the scope of claims included herein.

EXAMPLE

Example 1

270 g of styrene, 710 g of 1,3-butadiene, 5,000 g of n-hexane, and 0.8 g of 2,2-bis(2-oxolanyl)propane as a polar additive were added to a 20 L autoclave reactor and an inner temperature of the reactor was elevated to 40° C. When the inner temperature of the reactor reached 40° C., 4 mmol of n-butyl lithium was added to the reactor and an adiabatic temperature-rising reaction was performed until the reaction was stabilized. About 20 minutes after the adiabatic temperature-rising reaction was finished, 20 g of 1,3-butadiene was added to the reactor. After 5 minutes, 5 mmol of 3-dimethylamino-2-((dimethylaminomethyl)propyl) trimethoxysilane was added as a modifying agent to the reactor and reaction was performed for 15 minutes. Then, reaction was stopped using ethanol and 5 ml of a 0.3 wt % solution of butylated hydroxytoluene (BHT) as an antioxidant in hexane was then added to the reaction mixture.

The polymerization product was stirred in warm water heated by steam to remove the solvent and the resulting solution was then roll-dried to remove the residual solvent and water, thereby preparing a modified conjugated diene polymer. Analysis results of the modified conjugated diene polymer thus prepared are shown in the following Table 1.

Example 2

A modified conjugated diene polymer was prepared in the same manner as in Example 1, except that 3 mmol of 3-dimethylamino-2-((dimethylaminomethyl)propyl) trimethoxysilane was added as a modifying agent. Analysis results of the modified conjugated diene polymer are shown in the following Table 1.

Example 3

A modified conjugated diene polymer was prepared in the same manner as in Example 1, except that that 3-dimethylamino-2-((dimethylaminomethyl)propyl) triethoxysilane was added instead of the 3-dimethylamino-2-((dimethylaminomethyl)propyl) trimethoxysilane as a modifying agent. Analysis results of the modified conjugated diene polymer are shown in the following Table 1.

Comparative Example 1

Analysis results of an unmodified conjugated diene polymer (2550-H, produced by LG Chem., Ltd., Korea) are shown in the following Table 1.

Comparative Example 2

A modified conjugated diene polymer was prepared in the same manner as in Example 1, except that dimethyldichlorosilane was added as a coupling agent, instead of the 3-dimethylamino-2-((dimethylaminomethyl)propyl)trimethoxysilane. Analysis results of the modified conjugated diene polymer are shown in the following Table 1.

[Test Example]

Analysis of conjugated diene polymers prepared in Example 1 to 3 and Comparative Examples 1 to 2 was performed in accordance with the following method.

a) Mooney viscosity: measured at 100° C. for 4 minutes using MV-2000 produced by ALPHA Technologies and two specimens having a weight of 15 g or more after pre-heating for one minute.

b) Gel permeation chromatography (GPC): GPC analysis was performed at 40° C. to determine molecular weight and molecular weight distribution of the obtained polymer. The column herein used was a combination of two PLgel Olexis columns produced by Polymer Laboratories and one PLgel mixed-C column. All newly replaced columns were mixed bed-type columns. In addition, polystyrene (PS) was used as a GPC standard material for determination of molecular weight. As a result of analysis, number average molecular weight (Mn), weight average molecular weight (Mw) and polydispersity were determined.

TABLE 1

| | | Examples | | | Comparative Examples | |
|---|---|---|---|---|---|---|
| Items | | 1 | 2 | 3 | 1 | 2 |
| Sample | | A | B | C | D | E |
| n-butyllithium (mmol) | | 4 | 4 | 4 | 4– | 4 |
| Polar additive (g) | | 0.8 | 0.8 | 0.8 | 0.8 | 0.8 |
| Modifying agent | a* | 5 | 3 | — | — | — |
| (mmol) | b* | — | — | 5 | — | — |
| Coupling agent | c | — | — | — | — | 1.2 |
| TDAE oil | Phr | — | — | — | 37.5 | — |
| Mooney viscosity (MV) | | 62 | 68 | 60 | 61 | 64 |
| NMR (%) | SM | 26 | 26 | 26 | 26 | 27 |
| | Vinyl | 42 | 43 | 42 | 49 | 43 |
| GPC (×10⁴) | Mn | 30 | 29 | 30 | 47 | 31 |
| | Mw | 38 | 43 | 37 | 98 | 39 |
| | PDI | 1.3 | 1.5 | 1.2 | 2.1 | 1.2 |

Note)
a: 3-dimethylamino-2-((dimethylaminomethyl)propyl)trimethoxysilane
b: 3-dimethylamino-2-((dimethylaminomethyl)propyl)triethoxysilane
c: dimethyldichlorosilane
NMR: Proton Nuclear Magnetic Resonance ($^1$H-NMR)
SM: Styrene monomer
Vinyl: 1,3-butadiene as vinyl monomer

TABLE 2

| (Unit: parts by weight) | S-1 | S-2 |
|---|---|---|
| Rubber | 100.0 | 137.5 |
| Silica | 70.0 | 70.0 |
| Coupling agent | 11.02 | 11.2 |
| Oil | 33.75 | — |
| Zinc oxide | 3.0 | 3.0 |
| Stearic acid | 2.0 | 2.0 |
| Antioxidant | 2.0 | 2.0 |
| Anti-aging agent | 2.0 | 2.0 |
| Wax | 1.0 | |
| Rubber accelerator | 1.75 | 1.75 |
| Sulfur | 1.5 | 1.5 |
| Vulcanization accelerator | 2.0 | 2.0 |
| Total weight | 230.2 | 234.0 |

Samples A, B and C shown in Table 1 as rubber raw materials were mixed under mixing conditions shown in Table 2 above to prepare conjugated diene polymer rubber compositions. The samples A and C were mixed under mixing conditions of S-1 and the sample B was mixed under mixing conditions of S-2.

Kneading of the rubber compositions of the conjugated diene polymers will be described as follows. In primary kneading, a rubber raw material (conjugated diene polymer), a filler, an organosilane coupling agent, an oil, zinc oxide, a stearic acid antioxidant, an anti-aging agent, a wax and accelerators were kneaded at 80 rpm using a Banbury mixer equipped with a temperature controller. At this time, the temperature of the kneader was controlled and a primary mixture was obtained at a discharge temperature of 140 to 150° C. In secondary kneading, after the primary mixture was cooled to room temperature, a rubber, sulfur and a vulcanization accelerator were added to the kneader and a secondary mixture was obtained at a discharge temperature of 45 to 60° C. In tertiary kneading, the secondary mixture was molded and was vulcanized using a vulcanization press at 180° C. for T90+10 minutes to prepare vulcanized rubbers. Physical properties of the prepared vulcanized rubbers were measured in accordance with the following method.

1) Tensile Strength Test

Tensile strength at break and tensile stress at an elongation of 300% (300% modulus) of specimens were measured by tensile strength testing in accordance with ASTM (American Society for Testing and Materials) 412.

2) Viscoelasticity

A dynamic mechanical analyzer produced by TA Instrument was used. Tan δ was measured while changing strain in a torsional mode at a frequency of 10 Hz and at different measurement temperatures of 0 to 60° C. Payne effect was represented as a difference between a minimum and a maximum at a strain of 0.2% to 40%. As Payne effect decreases, dispersibility of a filler such as silica is improved. As Tan δ at a low temperature of 0° C. increases, wet skid resistance is improved, and as Tan δ at a high temperature of 60° C. decreases, hysteresis loss decreases, and rolling resistance of tires decreases, that is, fuel consumption thereof is reduced. Physical properties of the vulcanized rubbers are shown in the following Table 3.

TABLE 3

| Items | Ex. 4 | Ex. 5 | Ex. 6 | Comp. Ex. 3 | Comp. Ex. 4 |
|---|---|---|---|---|---|
| Samples | A | B | C | D | E |
| 300% modulus (Kgf/cm$^2$) | 123 | 123 | 122 | 110 | 96 |
| Tensile strength (Kgf/cm$^2$) | 189 | 192 | 188 | 191 | 174 |
| Tan δ at 0° C. | 0.883 | 0.881 | 0.851 | 0.791 | 0.497 |
| Tan δ at 60° C. | 0.062 | 0.064 | 0.066 | 0.085 | 0.096 |
| ΔG' at 60° C. (Payne effect) | 0.34 | 0.34 | 0.35 | 0.64 | 0.95 |

As can be seen from results of Table 3 above, the modified conjugated diene polymer rubber compositions according to Examples 4 to 6 exhibited a great increase in 300% modulus (tensile stress) and a high Tan δ at 0° C., as compared to Comparative Examples 3 and 4, which indicates that tires comprising the modified conjugated diene polymers exhibited great improvement of wet skid resistance.

In addition, the modified conjugated diene polymers of Examples 4 to 6 according to the present invention exhibited a low Tan δ at 60° C., as compared to Comparative Examples 3 and 4. Tires comprising the modified conjugated diene polymers exhibited low rolling resistance as compared to the related art.

In addition, the modified conjugated diene polymers according to Examples 4 to 6 according to the present invention exhibited a low Payne effect (ΔG') at 60° C., as compared to Comparative Examples 3 and 4. From this result, it could be seen that dispersaiblity of silica was greatly improved.

What is claimed is:

1. A modified conjugated diene polymer represented by the following Formula 1:

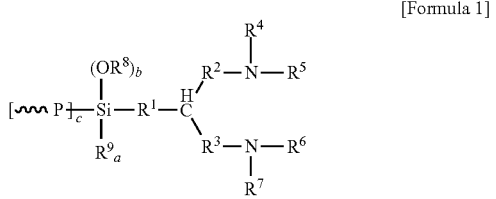

[Formula 1]

wherein $R^1$, $R^2$ and $R^3$ represent an alkylene group (—(CH$_2$)$_n$—, n=1~15), $R^4$, $R^5$, $R^6$, $R^7$ and $R^9$ each independently represent an alkyl group or an alkylsilyl group, $R^8$ represents a C$_1$-C$_{15}$ alkyl group and P is a conjugated diene polymer chain, and a is an integer of 0 to 2, b is an integer of 0 to 2 and c is an integer of 1 to 3 with the proviso that a+b+c equals 3.

2. The modified conjugated diene polymer according to claim 1, wherein the conjugated diene polymer chain is a random copolymer chain comprising an conjugated diene monomer and an aromatic vinyl monomer.

3. The modified conjugated diene polymer according to claim 1, wherein the modified conjugated diene polymer has a number average molecular weight of 1,000 to 2,000,000 g/mol.

4. The modified conjugated diene polymer according to claim 1, wherein the modified conjugated diene polymer has a vinyl content of 25% or more.

5. The modified conjugated diene polymer according to claim 1, wherein the modified conjugated diene polymer chain comprises 0.0001 to 40% by weight of the aromatic vinyl monomer, based on 100% by weight in total of the conjugated diene monomer and the aromatic vinyl monomer.

6. The modified conjugated diene polymer according to claim 1, wherein the modified conjugated diene polymer has a Mooney viscosity of 40 or more.

7. A method for preparing a modified conjugated diene polymer comprising:
(a) polymerizing a conjugated diene monomer, or a mixture of the conjugated diene monomer and an aromatic vinyl monomer in the presence of a solvent containing an organometallic compound to prepare an active conjugated diene polymer chain having a metal end; and
(b) modifying the active conjugated diene polymer chain with a compound represented by the following Formula 2 as a modifying agent:

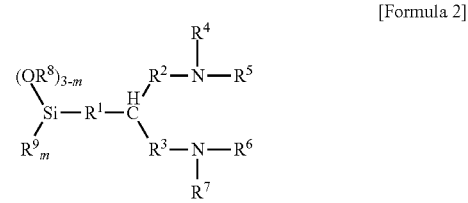

[Formula 2]

wherein $R^1$, $R^2$ and $R^3$ represent an alkylene group (—(CH$_2$)$_n$—, n=1~15), $R^4$, $R^5$, $R^6$, $R^7$ and $R^9$ each independently represent an alkyl group or an alkylsilyl group, $R^8$ represents a C$_1$-C$_{15}$ alkyl group and m is an integer of 0 to 2.

8. The method according to claim 7, wherein the organometallic compound is used in an amount of 0.01 to 10 mmol, based on 100 g in total of the monomer.

9. The method according to claim 7, wherein a molar ratio of the organometallic compound to the compound represented by Formula 2 is 1:0.1 to 1:10.

10. The method according to claim 7, wherein the polymerization further comprises adding a polar additive.

11. The method according to claim 10, wherein the polar additive is added in an amount of 0.001 to 50 g, based on 100 g in total of the monomer.

12. A modified conjugated diene polymer prepared by the method according to claim 7.

13. A rubber composition comprising 0.1 to 200 parts by weight of a reinforcing filler with respect to 100 parts by weight of the modified conjugated diene polymer according to claim 6.

14. The rubber composition according to claim 13, wherein the rubber composition comprises:
100 parts by weight of a polymer mixture of 10 to 100% by weight of the modified conjugated diene polymer and 0 to 90% by weight of another rubber;
5 to 200 parts by weight of silica; and
2 to 20 parts by weight of a silane coupling agent.

15. The rubber composition according to claim 13, wherein the rubber composition further comprises 0.1 to 100 parts by weight of carbon black.

16. The rubber composition according to claim 13, wherein the reinforcing filler is a silica filler.

17. A tire comprising the rubber composition according to claim 13.

18. A modifying agent comprising a compound represented by the following Formula 2:

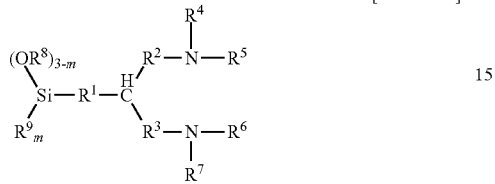

[Formula 2]

wherein $R^1$, $R^2$ and $R^3$ represent an alkylene group ($-(CH_2)_n-$, n=1~15), $R^4$, $R^5$, $R^6$, $R^7$ and $R^9$ each independently represent an alkyl group or an alkylsilyl group, $R^8$ represents a $C_1$-$C_{15}$ alkyl group and m is an integer of 0 to 2.

* * * * *